United States Patent [19]

Mayer

[11] 4,218,141
[45] Aug. 19, 1980

[54] VAPOR ANALYSIS TEST TUBE

[75] Inventor: Peter Mayer, Müllheim, Fed. Rep. of Germany

[73] Assignee: Hellma GmbH & Co. KG, Müllheim, Fed. Rep. of Germany

[21] Appl. No.: 969,738

[22] Filed: Dec. 15, 1978

[30] Foreign Application Priority Data

May 26, 1978 [DE] Fed. Rep. of Germany ....... 2823138

[51] Int. Cl.² .................. G01J 3/00; G01N 21/00
[52] U.S. Cl. ............................ 356/246; 73/27 R; 73/421.5 R
[58] Field of Search .................. 73/27 R, 343 B; 350/319, 246

[56] References Cited

U.S. PATENT DOCUMENTS

| 197,156 | 11/1877 | Meyer | 73/343 B |
|---|---|---|---|
| 2,269,850 | 1/1942 | Hebler | 73/27 R |
| 2,505,037 | 4/1950 | Frumkin | 73/343 B |
| 2,512,857 | 6/1950 | Gow | 73/27 R |
| 3,075,379 | 1/1963 | Schmauch | 73/27 R |
| 3,100,985 | 8/1963 | Wells | 73/27 R |
| 3,138,436 | 6/1964 | Harmon | 73/27 R X |
| 3,867,042 | 2/1975 | Mayer et al. | 356/246 |
| 3,877,817 | 4/1975 | Ralston | 356/319 X |
| 3,918,817 | 11/1975 | Posgate | 356/246 X |

Primary Examiner—Daniel M. Yasich
Attorney, Agent, or Firm—Peter K. Kontler

[57] ABSTRACT

A cuvette whose outer side has a recess for a flat square resistance thermometer which is bonded to a thin partition between the recess and the internal space of the cuvette. The thermometer is connected with a device which indicates the temperature of a sample in the cuvette and/or which regulates the temperature of the sample if such temperature deviates from an optimum value. The contacts of the thermometer are soldered to the corresponding conductors of a cable. The joint between the contacts and the conductors as well as the thermometer and its contacts are confined in the recess by a mass of epoxy resin. The thickness of the partition is a fraction of one millimeter, and the thermometer is bonded to the outer side of the partition by a heat-conducting adhesive.

20 Claims, 2 Drawing Figures

VAPOR ANALYSIS TEST TUBE

BACKGROUND OF THE INVENTION

The present invention relates to vessels in general, and more particularly to improvements in cuvettes, especially in tubes for use in photometric or spectroscopic examination of samples of liquid or gaseous media which must be tested at a predetermined temperature or within a predetermined temperature range.

It is known to test one or more characteristics of media in a cuvette by resorting to a photometric or spectrophotometric apparatus. In many instances, the samples must be tested at a given temperature or within a predetermined and often rather narrow temperature range. The establishment and maintenance of such conditions (optimum temperature or a narrow temperature range) is necessary for a number of reasons, for example, to avoid changes in the aggregate state of media as a result of temperature changes prior to or during testing.

OBJECTS AND SUMMARY OF THE INVENTION

An object of the invention is to provide a vessel, especially a cuvette, with a thermometer or temperature sensor which is constructed and mounted in such a way that it can furnish accurate and reliable readings as to the temperature of the medium or sample in the cuvette but is adequately separated from the medium or sample to avoid any contact therebetween.

Another object of the invention is to provide a cuvette wherein the thermometer is installed in such a way that the tube can be used for testing of a wide variety of samples without affecting the accuracy of temperature measurements.

A further object of the invention is to provide a cuvette which can be used for photometric or spectographic examination of samples with continuous indication and/or regulation of the temperature of a sample in the cuvette and which can be mass produced at a reasonable cost.

An additional object of the invention is to provide a cuvette wherein the thermometer can be used for indication and/or continuous or intermittent regulation of the temperature of a sample in the interior of the cuvette.

Another object of the invention is to provide a cuvette wherein the temperature measuring means is adequately shielded from the sample in the cuvette as well as from other substances which are likely to influence its measurements and/or indications.

A further object of the invention is to provide novel and improved means for connecting the thermometer with one or more devices for furnishing visible or otherwise detectable indications of the measured temperature of a sample in the cuvette.

The invention is embodied in a cuvette for examination of media or samples at a given temperature, particularly for photometric or spectrophometric examination of solid, liquid or gaseous media. The cuvette comprises wall means and at least one thermometer which is at least partly embedded in the wall means of the cuvette. In accordance with a presently preferred embodiment of the invention, the outer side of the wall means of the cuvette has a recess which is separated from the inner side of the wall means by a relatively thin portion or partition of the wall means (the thickness of such wall portion may be a fraction of one millimeter, e.g., 0.5 mm), and the thermometer is installed in such recess. For example, the thermometer may constitute a relatively thin flat polygonal body which is secured to the wall portion by a heat-conducting adhesive, preferably an adhesive which contains a relatively high percentage of silver. It is further preferred to provide means for confining the thermometer in the recess, for example, a mass of epoxy resin which fills the recess and shields the thermometer from external influences and/or mechanical damage.

The placing of the thermometer adjacent to and preferably in intimate contact with the relatively thin wall portion or partition which separates the recess from the medium or sample in the interior of the cuvette insures that the thermometer can accurately indicate the temperature of but is held out of direct contact with the medium, i.e., the medium cannot attack and/or contaminate the thermometer and the cuvette can be used for testing a wide variety of samples.

It is further within the purview of the invention to provide the outer side of the wall means of the cuvette with two or more spaced-apart recesses and to install a discrete thermometer in each recess. The thermometer or thermometers may be used for mere indication of the temperature of media, or they may generate and transmit signals which are used to regulate the temperature of the medium, i.e., to maintain the temperature of the medium in the cuvette within a desired range. Since the wall portion between the recess and the inner side of the wall means is thin or very thin, the thermometer can furnish visible or other indications of the temperature of a medium in the cuvette practically without any delay, especially if it is secured to the wall portion by a heat-conducting adhesive. The aforementioned confining means (the presently preferred confining means is an epoxy resin) not only provides a highly satisfactory insulating action but also protects the thermometer from damage by mechanical means. Furthermore, the confining means insulates the corresponding (recessed) part of the wall means to insure that the temperature of the medium in the cuvette (at the inner side of the wall means) is not influenced by the temperature of the surrounding atmosphere and/or by the temperature of one or more parts which contact the outer side of the cuvette.

The novel features which are considered as characteristic of the invention are set forth in particular in the appended claims. The improved cuvette itself, however, both as to its construction and the mode of assembling and utilizing the same, together with additional features and advantages thereof, will be best understood upon perusal of the following detailed description of certain specific embodiments with reference to the accompanying drawing.

DESCRIPTION OF THE PREFERRED EMBODIMENTS

Figure 1:
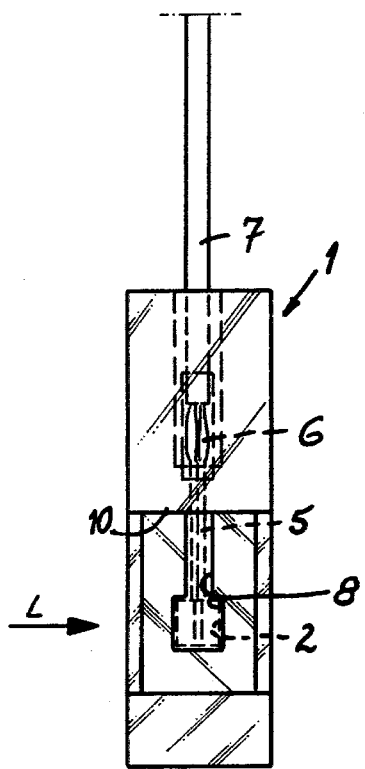
FIG. 1 is an end elevational view of a cuvette which embodies one form of the invention and is provided with a single thermometer.
Figure 2:
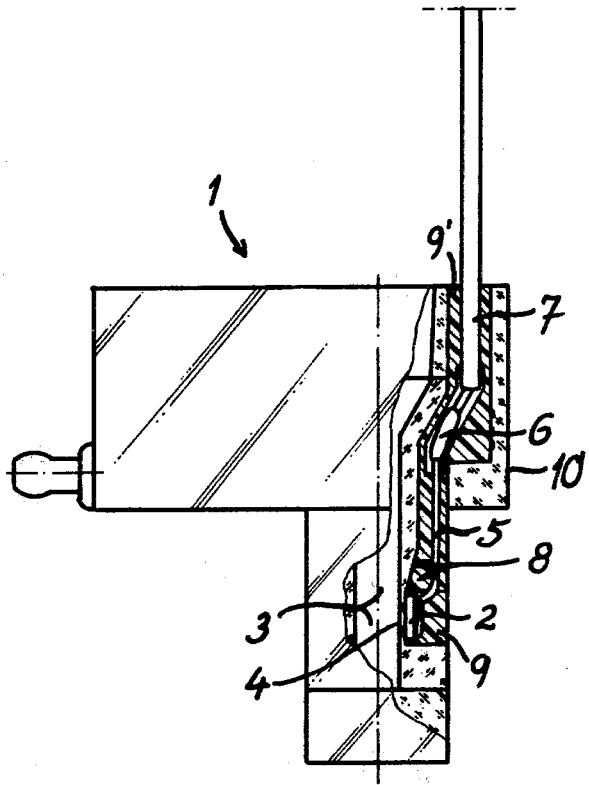
FIG. 2 is a side elevational view of the cuvette, with a portion of its wall means broken away.

The drawing shows a cuvette 1 with a thermometer 2 which is installed in the wall means of the cuvette. The wall means may consist of glass or another suitable material depending on the nature of the medium to be tested. The thermometer 2 is closely adjacent to but separated from the sample-receiving cavity or space 3 of the cuvette, i.e., from the inner side of the wall means of the cuvette. The thin wall portion or partition 4 between the thermometer 2 and the space 3 shields the thermometer from the medium in the cuvette 1; the thickness of such wall portion may be a small fraction of one millimeter, e.g., 0.5 mm. The material of the wall portion 4 is the same as the material of the remaining part or parts of the cuvette 1, and the thermometer 2 can react practically without any delay because the portion 4 is thin or extremely thin. Adequate shielding of the thermometer 2 from the material in the internal space 3 of the cuvette 1 is especially desirable when the medium to be examined or tested contains one or more aggressive ingredients which could damage or destroy the thermometer.

The thermometer 2 is secured to the outer side of the wall portion 4 by means of a suitable adhesive, preferably a heat-conducting adhesive which contains a relatively high percentage of silver. This insures a highly sensitive exchange of heat energy between the medium in the space 3 and the thermometer 2. The illustrated thermometer 2 is a resistance thermometer having electrical contacts 5 in the form of wires which extend upwardly from the thermometer to a junction 6 (preferably including joints consisting of solder) where the contacts are electrically connected to the conductor means of an electric cable 7. The cable 7 may be connected with a temperature indicating device of any known design or to a device which regulates the temperature of the wall means of the cuvette 1 (and hence the temperature of the medium in the space 3) when the measured temperature deviates from the desired temperature or temperature range. The just discussed device can also serve to regulate the temperature of a medium prior to introduction into the cuvette 1.

The outer side of the wall means of the cuvette 1 has an elongated recess means 8 including a deepmost lower section which accommodates the thermometer 2 and an upwardly extending section for the contacts 5 and the connecting means 6. Once the thermometer 2 and its contacts 5 are installed in the recess 8 and the contacts 5 are connected to the corresponding conductor means of the cable 7, as at 6, the recess 8 is filled with a mass 9 of epoxy resin which confines the parts 2, 5 and 6 and insulates the thermometer 2 from the surrounding atmosphere.

FIG. 1 shows that the thermometer 2 is a relatively flat polygonal body, preferably a square body having a length and width of a few millimeters (e.g., 4 mm) and a thickness which is a fraction of the length or width (e.g., 1 mm). As stated above, the reaction time of the thermometer 2 can be reduced by bonding one of its major surfaces to the outer side of the wall portion 4 by means of a heat-conducting adhesive, such as a paste containing a relatively high percentage of silver. The direction in which a beam of light or other radiation passes through the sample or medium in the space 3 of the cuvette 1 is indicated by the arrow L. The illustrated thermometer 2 may constitute a commercially available article, e.g., a resistance thermometer known on the market as PT 100. The installation of such thermometers in the recesses 8 of a series of cuvettes 1 and the filling of recesses with epoxy resin or another suitable confining material which is a good insulator and shields the thermometer against mechanical damage can be carried out by resorting to conventional mass production techniques.

As mentioned above, the contacts 5 and the junction 6 between such contacts and the conductor means of the cable 7 are located in a portion of the recess 8 which extends upwardly from the deepmost portion of the recess 8, namely, from that portion which accommodates the thermometer 2. At least a portion of the wall means of the tube 1, and more particularly at least a portion of that part of the wall means which is provided with the recess 8, is surrounded by a shroud 10 which is bonded to the cuvette 1 by a suitable adhesive. The shroud 10 shields the joint 6 and has a second recess which communicates with the recess 8 in the outer side of the wall means of the cuvette 1 and is also filled with a mass 9' of epoxy resin or another suitable confining material. The shroud 10 and the mass of confining material therein protect the joint 6 from mechanical damage.

An important advantage of the improved cuvette is that the thermometer 2 is adequately protected from the medium in the space 3 as well as at the other side thereof, that the thermometer 2 can immediately react to any changes in the temperature of a sample (as well as that it can indicate the temperature of the freshly introduced sample without any or with a minimum of delay), and that the entire device can be produced at a reasonable cost. Moreover, the thermometer 2 can be used to perform a variety of functions including mere measurement and indication of the temperature of a medium in the space 3 and the generation of signals which are used to regulate the temperature when the measured temperature deviates from a desirable temperature or temperature range.

The shroud 10 protects the joint 6, the contacts 5 and the cable 7 from external influences including bending, extraction, breakage, short circuiting and others.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

I claim:

1. A transparent cuvette for use in examination of media at a given temperature, particularly in photometric or spectrophotometric examination of media, comprising wall means configured to define a cavity on an inner side thereof for receiving a sample of a respective medium to be examined; and at least one thermometer means at least partly embedded in a recess means on an outer side of said wall means, said thermometer means being provided in and separated from said cavity by said wall means.

2. The cuvette of claim 1, wherein said wall means has said inner side, an outer side and said recess means in said outer side, said thermometer means being located in said recess means.

3. The cuvette of claim 2, wherein said wall means includes a relatively thin portion intermediate said inner side and said recess means and said thermometer means is immediately adjacent to said portion.

4. The cuvette of claim 3, wherein the thickness of said portion of said wall means is a fraction of one millimeter.

5. The cuvette of claim 3, further comprising means for securing said thermometer means to said portion of said wall means.

6. The cuvette of claim 5, wherein said securing means is a heat-conducting adhesive.

7. The cuvette of claim 6, wherein said adhesive contains silver.

8. The cuvette of claim 2, further comprising means for confining said thermometer means in said recess means.

9. The cuvette of claim 8, wherein said confining means fills said recess means.

10. The cuvette of claim 9, wherein said confining means is an epoxy resin.

11. The cuvette of claim 1, wherein said thermometer means is a resistance thermometer.

12. The cuvette of claim 11, wherein said thermometer means is a flat polygonal body.

13. The cuvette of claim 12, wherein said body is a square having a length and width of approximately 4 mm and a thickness of approximately 1 mm.

14. The cuvette of claim 1, said thermometer being located in said recess means and having a plurality of electric contacts, said recess means having a first section for said thermometer means and a second section communicating with said first section and receiving said contacts, and further comprising means for confining said thermometer means and said contacts in the respective sections of said recess means.

15. The cuvette of claim 14, further comprising cable means having conductor means and means for conductively connecting said conductor means with said contacts, said connecting means being located in said recess means and being surrounded by said confining means.

16. The cuvette of claim 15, wherein said connecting means is solder and said confining means is a mass of epoxy resin which fills said recess means.

17. The cuvette of claim 15, wherein said second section is located at a level above said first section of said recess means.

18. The cuvette of claim 15, further comprising a shroud for said connecting means, said shroud surrounding said wall means and at least a portion of said recess means.

19. The cuvette of claim 18, wherein said shroud is bonded to said wall means.

20. The cuvette of claim 18, wherein said shroud has a second recess in at least partial communication with said first mentioned recess means and said confining means fills said second recess.

* * * * *